(12) United States Patent
Bauhahn

(10) Patent No.: US 7,647,116 B2
(45) Date of Patent: Jan. 12, 2010

(54) CONTEXT-SENSITIVE COLLECTION OF NEUROSTIMULATION THERAPY DATA

(75) Inventor: Ruth E. Bauhahn, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 825 days.

(21) Appl. No.: 10/388,798

(22) Filed: Mar. 13, 2003

(65) Prior Publication Data

US 2004/0181262 A1 Sep. 16, 2004

(51) Int. Cl.
*A61N 1/08* (2006.01)
(52) U.S. Cl. .......................................... 607/48; 607/59
(58) Field of Classification Search .................. 607/30, 607/46, 48, 55–60, 63, 117, 118, 137
See application file for complete search history.

(56) References Cited

U.S. PATENT DOCUMENTS

| | | | | |
|---|---|---|---|---|
| 5,304,206 | A * | 4/1994 | Baker et al. ..................... | 607/2 |
| 5,716,382 | A * | 2/1998 | Snell ............................ | 607/30 |
| 5,938,690 | A * | 8/1999 | Law et al. ..................... | 607/46 |
| 6,234,964 | B1 * | 5/2001 | Iliff ............................. | 600/300 |
| 6,308,102 | B1 | 10/2001 | Sieracki et al. | |
| 6,381,496 | B1 * | 4/2002 | Meadows et al. ............. | 607/59 |
| 6,622,048 | B1 * | 9/2003 | Mann et al. ................... | 607/46 |
| 6,748,276 | B1 * | 6/2004 | Daignault et al. ............ | 607/46 |
| 2001/0007950 | A1 * | 7/2001 | North et al. .................. | 607/59 |
| 2002/0007249 | A1 | 1/2002 | Cranley et al. | |
| 2002/0032878 | A1 | 3/2002 | Karpf | |
| 2002/0035486 | A1 | 3/2002 | Huyn et al. | |
| 2002/0052540 | A1 | 5/2002 | Iliff | |
| 2002/0068857 | A1 | 6/2002 | Iliff | |
| 2002/0107824 | A1 | 8/2002 | Ahmed | |
| 2002/0133502 | A1 | 9/2002 | Rosenthal et al. | |
| 2002/0184050 | A1 * | 12/2002 | Papageorge .................... | 705/2 |

FOREIGN PATENT DOCUMENTS

WO    WO 00/28459    5/2000

OTHER PUBLICATIONS

Notification of Transmittal of the International Preliminary Report on Patentability for PCT/US2004/001989, dated Dec. 13, 2004 (8 pgs.).
Office Action dated Jan. 25, 2008 for related U.S. Appl. No. 11/331,388 (7 pgs.).

(Continued)

*Primary Examiner*—Mark W Bockelman
*Assistant Examiner*—Eric D Bertram
(74) *Attorney, Agent, or Firm*—Shumaker-Sieffert, P.A.

(57) ABSTRACT

Techniques for collection and management of data relating to neurostimulation therapy involve selection of questions for the user to answer based on the context of the therapy delivered by the neurostimulation device at the time the questions are presented. In this manner, appropriate data may be collected for specific contexts. The techniques may involve storage of answers to the questions with information indicative of the contexts. Information indicative of the contexts may include information relating to the types of neurostimulation therapy requests made by the patient, stimulation settings associated with the neurostimulation therapy, and data and time information. The techniques may be implemented by neurostimulation therapy interface device such as a patient programmer that controls operation of an implanted neurostimulation device.

50 Claims, 6 Drawing Sheets

OTHER PUBLICATIONS

European Office Action dated Nov. 10, 2008 for corresponding European Application No. 04 704 971.3-2310 (3 pgs.).
Responsive Amendment dated Apr. 23, 2008 for related U.S. Appl. No. 11/331,388 (13 pgs.).
Office Action dated Aug. 18, 2008 for related U.S. Appl. No. 11/331,388 (9 pgs.).
Responsive Amendment dated Oct. 7, 2008 for related U.S. Appl. No. 11/331,388 (11 pgs.).

* cited by examiner

CONTEXT-SENSITIVE COLLECTION OF NEUROSTIMULATION THERAPY DATA

TECHNICAL FIELD

The invention relates to neurostimulation devices and, more particularly, collection of information relating to neurostimulation therapy.

BACKGROUND

Neurostimulation therapy devices deliver therapy to treat a variety of symptoms or conditions, such as chronic pain, tremor, Parkinsons disease, or epilepsy. In general, a neurostimulation device delivers therapy in the form of electrical stimulation pulses. An implantable neurostimulation device, for example, delivers neurostimulation therapy via leads that include electrodes located proximate to the spinal cord or within the brain of a patient.

A clinician interacts with the implanted device using an external programmer to select values for a number of programmable parameters in order to configure the neurostimulation therapy to be delivered to the patient. For example, the clinician may select an amplitude and pulse width for a stimulation waveform to be delivered to the patient, as well as a rate at which the pulses are to be delivered to the patient. The clinician also may select particular electrodes to be used to deliver the pulses, and the polarities of the selected electrodes.

The clinician may rely on patient feedback to select optimum values for the parameters. The feedback may involve trial and error testing of different parameters followed by patient feedback concerning overall efficacy of the therapy. In particular, the patient feedback may provide information concerning the efficacy of the therapy in relieving symptoms and avoiding undesirable side effects. Ordinarily, testing to obtain patient feedback is performed in a clinical setting and can be time consuming.

SUMMARY

In general, the invention is directed to techniques for collection and management of information relating to operation of an implantable neurostimulation device and efficacy of neurostimulation therapy based on user input. The techniques may involve selection of questions for the user to answer based on the context of the therapy delivered by the neurostimulation device at the time the questions are presented. In this manner, appropriate data may be collected on a timely basis for specific contexts, e.g., specific therapy settings, symptoms, or patient events or activities. The neurostimulation therapy may treat pain, movement disorders or other health problems.

The techniques may involve storage of answers to the questions with information indicative of the associated contexts. Information indicative of the contexts may include information relating to the types of neurostimulation therapy requests made by the patient, stimulation settings associated with the neurostimulation therapy, and date and time information. The techniques may be implemented by a neurostimulation therapy interface device, such as a patient programmer that controls operation of an implanted neurostimulation device. In some embodiments, the patient programmer may be a portable, handheld device carried by the patient.

In one embodiment, the invention provides a method comprising receiving a neurostimulation therapy request from a patient, selecting one or more questions based on a context associated with the request, and presenting the selected questions to the patient.

In another embodiment, the invention provides a device comprising an input medium that receives a neurostimulation therapy request from a patient, a processor that selects one or more questions based on a context associated with the request, and an output medium that presents the selected questions to the patient.

In a further embodiment, the invention provides a computer-readable medium comprising instructions to cause processor to receive a neurostimulation therapy request from a patient, select one or more questions based on a context associated with the request, and present the selected questions to the patient.

In an added embodiment, the invention provides a method comprising receiving a neurostimulation therapy request from a patient, directing delivery of a response to the request, selecting one or more questions based on a context associated with the request, receiving answers to the selected questions from the patient, and storing information relating to the answers, a context associated with the requests, and one or more settings associated with the neurostimulation therapy.

The invention may provide a number of advantages. For example, the techniques described herein may offer effective collection of diagnostic data in the context of patient usage of neurostimulation therapy. In this manner, the data can be correlated with a patient's schedule and activities, and with particular disease states and associated characteristics. In addition, the data can be collected throughout the course of a patient's daily routine, e.g., via a handheld patient programmer device. The data may offer greater precision and be used to build a base of clinical information for use by the clinician in establishing improved neurostimulation therapy efficacy.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
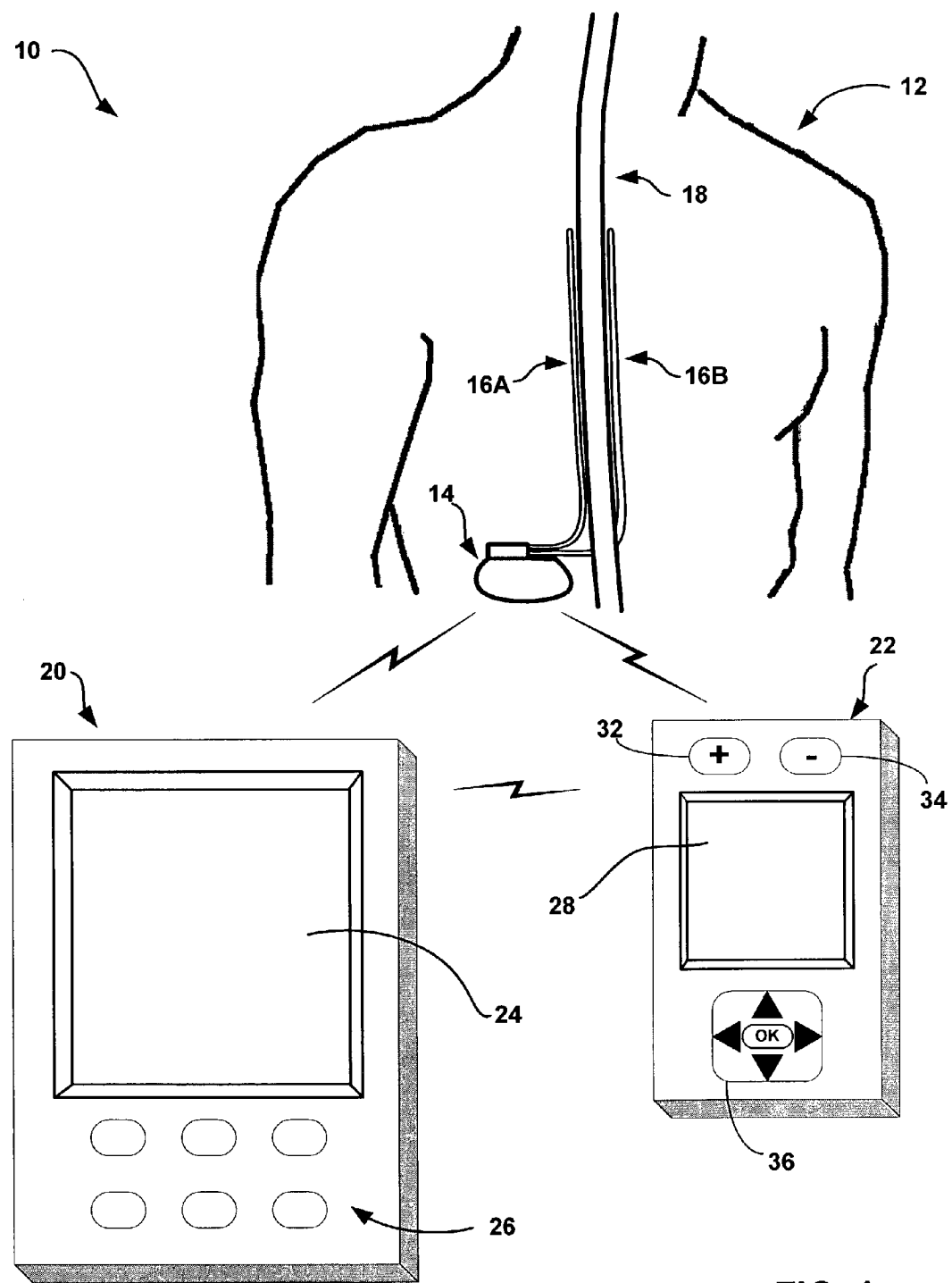
FIG. 1 is a diagram illustrating an example system for delivery of neurostimulation therapy and context-sensitive collection of neurostimulation device data.

FIG. 1 is a diagram illustrating an example system 10 for delivery of neurostimulation therapy to a patient 12 and context-sensitive collection of neurostimulation device data. As shown in FIG. 1, system 10 includes an implantable medical device 14 that delivers neurostimulation therapy to patient 12. IMD 14 may be an implantable pulse generator, and may deliver neurostimulation therapy to patient 12 in the form of electrical pulses. IMD 14 may be configured to deliver neurostimulation therapy for treatment of pain. Alternatively, IMD 12 may deliver neurostimulation therapy for treatment of movement disorders.

IMD 12 delivers neurostimulation therapy to patient 12 via leads 16A and 16B (collectively "leads 16"). Leads 16 may, as shown in FIG. 1, be implanted proximate to the spinal cord 18 of patient 12, and IMD 12 may deliver spinal cord stimulation (SCS) therapy to patient 12 in order to, for example, reduce pain experienced by patient 12. However, the invention is not limited to the configuration of leads 16 shown in FIG. 1 or the delivery of SCS therapy. For example, one or more leads 16 may extend from IMD 14 to the brain (not shown) of patient 12, and IMD 14 may deliver deep brain stimulation (DBS) therapy to patient 12 to treat, for example, movement disorders such as tremor or epilepsy.

System 10 also includes a clinician programmer 20 and a patient programmer 22. Clinician programmer 20 may, as shown in FIG. 1, be a handheld computing device. Clinician programmer 20 includes a display 24, such as a LCD or LED display, to display information to a user, e.g., a clinician. Clinician programmer 20 may also include a keypad 26, which may be used by a user to interact with clinician programmer 20. In some embodiments, display 24 may be a touch screen display, and a user may interact with clinician programmer 20 via display 24. A user may also interact with clinician programmer 20 using peripheral pointing devices, such as a stylus or mouse. Keypad 26 may take the form of an alphanumeric keypad or a reduced set of keys associated with particular functions.

A clinician (not shown) may use clinician programmer 20 to program neurostimulation therapy for patient 12. For example, the clinician may select existing programs or specify programs by selecting program parameter values, and test the selected or specified programs on patient 12. The clinician may receive feedback from patient 12, and store the programs and rating information associated with the programs. As will be described, system 10 may support context-sensitive collection of neurostimulation therapy data based on patient input, permitting the clinician to formulate more effective programs for delivery of neurostimulation therapy for patient 12.

Like clinician programmer 20, patient programmer 22 may be a handheld computing device. Patient programmer 22 may also include a display 28 and input keys 32, 34, 36 to allow patient 12 to interact with patient programmer 22. In this manner, patient programmer 22 provides patient 12 with a neurostimulation therapy interface device. For example, input keys 32, 34 may be depressed by patient 12 to request an increase or decrease, respectively, in stimulation settings. Input key 36 may permit navigation within display 28. In some embodiments, display 28 may be a touch screen display, and patient 12 may interact with patient programmer 22 via display 28. Patient 12 may also interact with patient programmer 22 using peripheral pointing devices, such as a stylus or mouse. Patient programmer 22 may be sized for ease of portability, permitting patient 12 to carry the patient programmer during the patient's daily routine.

Patient 12 may use patient programmer 22 to control the delivery of neurostimulation therapy by IMD 14. Patient 12 may use patient programmer 22 to enter neurostimulation therapy requests. For example, patient 12 may use patient programmer 22 to start, stop or adjust neurostimulation therapy. In particular, patient programmer 22 may permit patient 12 to adjust stimulation settings such as duration, amplitude, pulse width and pulse rate, either directly or indirectly. Patient 12 may adjust stimulation settings indirectly, for example, by selecting particular programs that specify combinations of stimulation settings, as well as electrode combinations.

To aid in collection of neurostimulation therapy data, patient programmer 22 may present one or more context-sensitive questions to patient 12. For example, patient programmer 22 may select one or more context-sensitive questions based on a context associated with a neurostimulation request made by the patient. Accordingly, patient programmer 22 may be responsive to entry of a neurostimulation request such as a request to start, stop or adjust neurostimulation therapy. Alternatively, patient programmer 22 may be configured to periodically present a set of context-sensitive questions based on the current context of the neurostimulation therapy delivered by device 14.

The questions may be context-sensitive in the sense that patient programmer 22 selects them in response to the context presented by the neurostimulation therapy or the neurostimulation therapy request entered by patient 12 via the patient programmer. A clinician may formulate a set of questions, and then device selection criteria for selection of the questions based on context. For a given context, patient programmer 22 selects one or more of the questions formulated by the clinician, e.g., from a memory associated with the patient programmer, and presents the selected questions to patient 12.

Patient programmer 22 receives answers to the context-sensitive questions from patient 12, and stores the questions for analysis by a clinician. Patient programmer 22 may store information relating to the answers, a context associated with the neurostimulation requests made by patient 12, and one or more settings associated with the neurostimulation therapy. In addition, the stored information may include a data and time stamp. In this manner, the clinician may analyze the patient's answers associated with particular contexts during the course of delivery of neurostimulation therapy to patient 12, as well as the time at which the contexts arise during the patient's daily routine. The wealth and specificity of the information may be helpful to the clinician in formulating neurostimulation therapy appropriate for the patient's condition and routine.

The contextual data may include a variety of data entered by the user, as well as operational data obtained from IMD 14 by patient programmer 22. The contextual data may include, for example, the type of neurostimulation therapy request made by patient 12, e.g., start, stop, adjust, the stimulation settings applicable to the patient at the time of the request such as amplitude, pulse width, pulse width, and duration, the date and time, the patient's activity level, the level of pain or relief perceived by the patient (in the event the neurostimulation therapy is directed to pain symptoms), the location of pain experienced by the patient, qualitative aspects of the pain such as sharpness or throbbing, intake of medication coincident with the neurostimulation therapy, and the like.

Patient programmer 22 may allow patient 12 greater control over the delivery of neurostimulation therapy within limits set by the clinician, and may lead to more effective therapy and efficient use of clinician time. Patient 12 may be able to make neurostimulation therapy requests to stop and start stimulation by IMD 14, and select or adjust stimulation settings. Patient 12 may make the neurostimulation requests in order to address changes in symptoms, which may occur throughout the day, or based on changes in the position, posture, or activity of the patient.

These modifications and improvements to neurostimulation therapy may occur without clinician intervention. Further, the clinician may be able to spend less time initially programming neurostimulation therapy for patient 12 by providing a variety of different programs at implant from which patient 12 may choose. The programs may specify different stimulation settings and allow patient 12 to experiment with, and optimize, improve, or tailor the neurostimulation therapy over time. Patient programmer 22 programs IMD 14 based on the requests to control the delivery of neurostimulation therapy to patient 12. In this manner, IMD 14 may deliver and adjust neurostimulation therapy in response to user input.

In conjunction with the neurostimulation therapy requests, patient programmer 22 opportunistically generates one or more questions for patient 12. Again, patient programmer 22 may be configured to select the questions from a larger set of questions formulated by the clinician. Patient programmer 22 selects the questions based on the context indicated by the neurostimulation therapy request made by patient 12, and advantageously stores the answers to the questions with data indicative of the context. Accordingly, the clinician can retrieve the stored information to better evaluate the patient's condition and needs.

IMD 14, clinician programmer 20 and patient programmer 22 may, as shown in FIG. 1, communicate via wireless communication. Clinician programmer 20 and patient programmer 22 may, for example, communicate via wireless communication with IMD 14 using RF telemetry techniques known in the art. Clinician programmer 20 and patient programmer 22 may communicate with each other using any of a variety of local wireless communication techniques, such as RF communication according to the 802.11 or Bluetooth specification sets, infrared communication according to the IRDA specification set, or other standard or proprietary telemetry protocols. Clinician programmer 20 and patient programmer 22 need not communicate wirelessly, however. For example, programmers 20 and 22 may communicate via a wired connection, such as via a serial communication cable, or via exchange of removable media, such as magnetic or optical disks, or memory cards or sticks.

Figure 2:
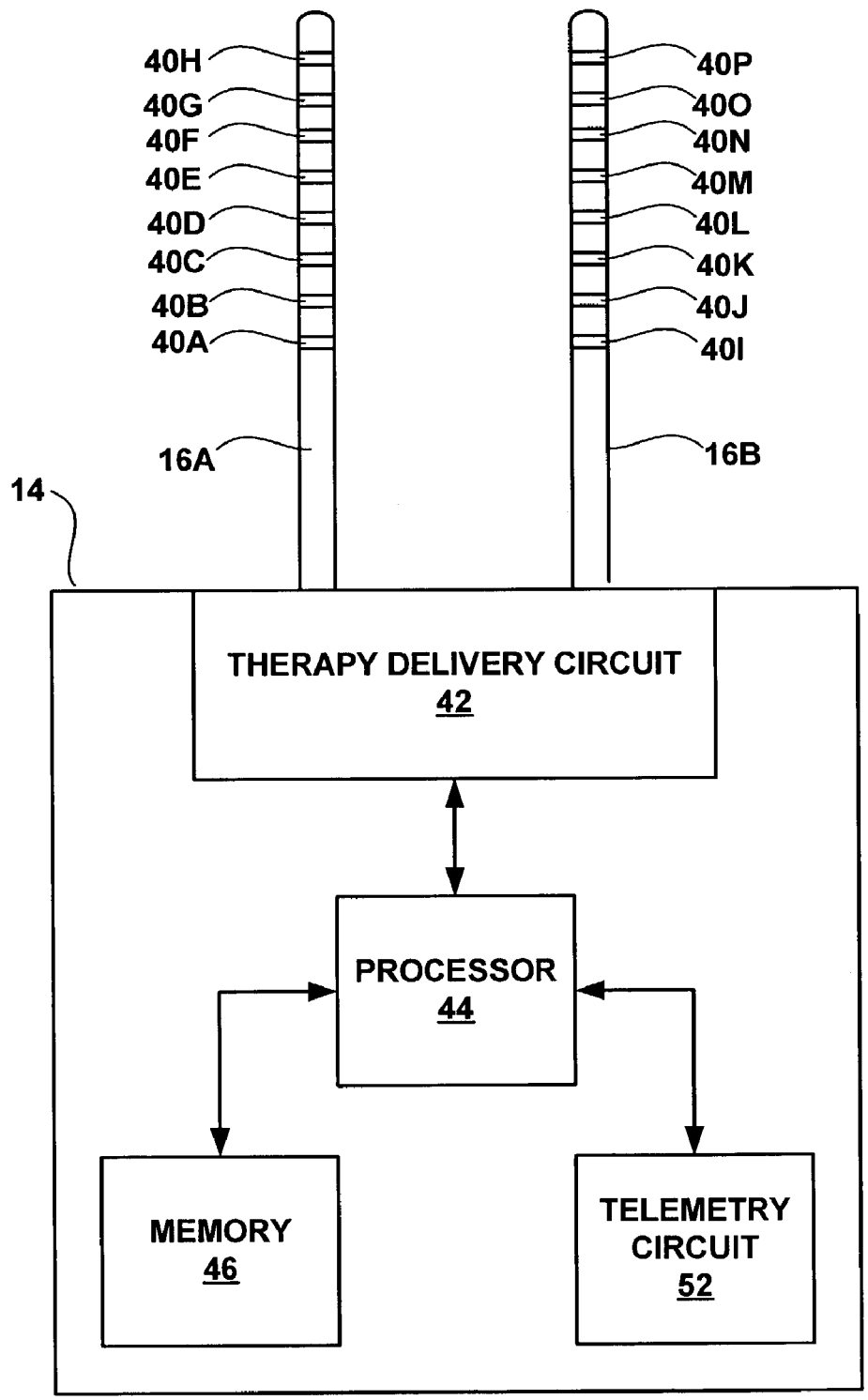
FIG. 2 is a block diagram illustrating an example implantable medical device for delivering neurostimulation therapy to a patient.

FIG. 2 is a block diagram illustrating an example configuration of IMD 14. IMD 14 may deliver neurostimulation therapy via electrodes 40A-H of lead 16A and electrodes 40I-P of lead 16B (collectively "electrodes 40"). Electrodes 40 may be ring electrodes. The configuration, type and number of electrodes 40 illustrated in FIG. 2 are merely exemplary.

Electrodes 40 are electrically coupled to a therapy delivery circuit 42 via leads 16. Therapy delivery circuit 42 may, for example, include an output pulse generator coupled to a power source such as a battery. Therapy delivery circuit 42 may deliver electrical pulses to patient 12 via at least some of electrodes 40 under the control of a processor 44.

Processor 44 controls therapy delivery circuit 42 to deliver neurostimulation therapy according to a selected parameter set. Specifically, processor 44 may control circuit 42 to deliver electrical pulses with the amplitudes and widths, and at the rates specified by the programs of the selected parameter set.

Processor 44 may also control circuit 42 to deliver the pulses via a selected subset of electrodes 40 with selected polarities, as specified by the programs of the selected parameter set. Processor 44 may control circuit 42 to deliver each pulse according to a different program of the parameter set. Processor 44 may include a microprocessor, a controller, a DSP, an ASIC, an FPGA, discrete logic circuitry, or the like.

IMD 14 also includes a memory 46. In some embodiments, memory 46 may store stimulation programs that are available to be selected by patient 12 for delivery of neurostimulation therapy. In some embodiments, processor 44 may record usage information and store the usage information in memory 46. Memory 46 may also include program instructions that, when executed by processor 44, cause IMD 14 to deliver neurostimulation therapy. Memory 46 may include any volatile, non-volatile, magnetic, optical, or electrical media, such as a RAM, ROM, CD-ROM, hard disk, removable magnetic disk, memory cards or sticks, NVRAM, EEPROM, flash memory, and the like.

IMD 14 also includes a telemetry circuit 52 that allows processor 44 to communicate with clinician programmer 20 and patient programmer 22. Processor 44 may receive programs to test on patient 12 from clinician programmer 20 via telemetry circuit 52 during programming by a clinician. Where IMD 14 stores stimulation programs in memory 46, processor 44 may receive the programs from clinician programmer 20 via telemetry circuit 52 during programming by a clinician, and later receive neurostimulation therapy requests made by patient 12 from patient programmer 22 via telemetry circuit 52. The neurostimulation therapy requests may include requests to start, stop or adjust stimulation settings. In some embodiments, patient programmer 22 may store the stimulation programs, and transmit them to IMD 14 via telemetry circuit 52.

Figure 3:
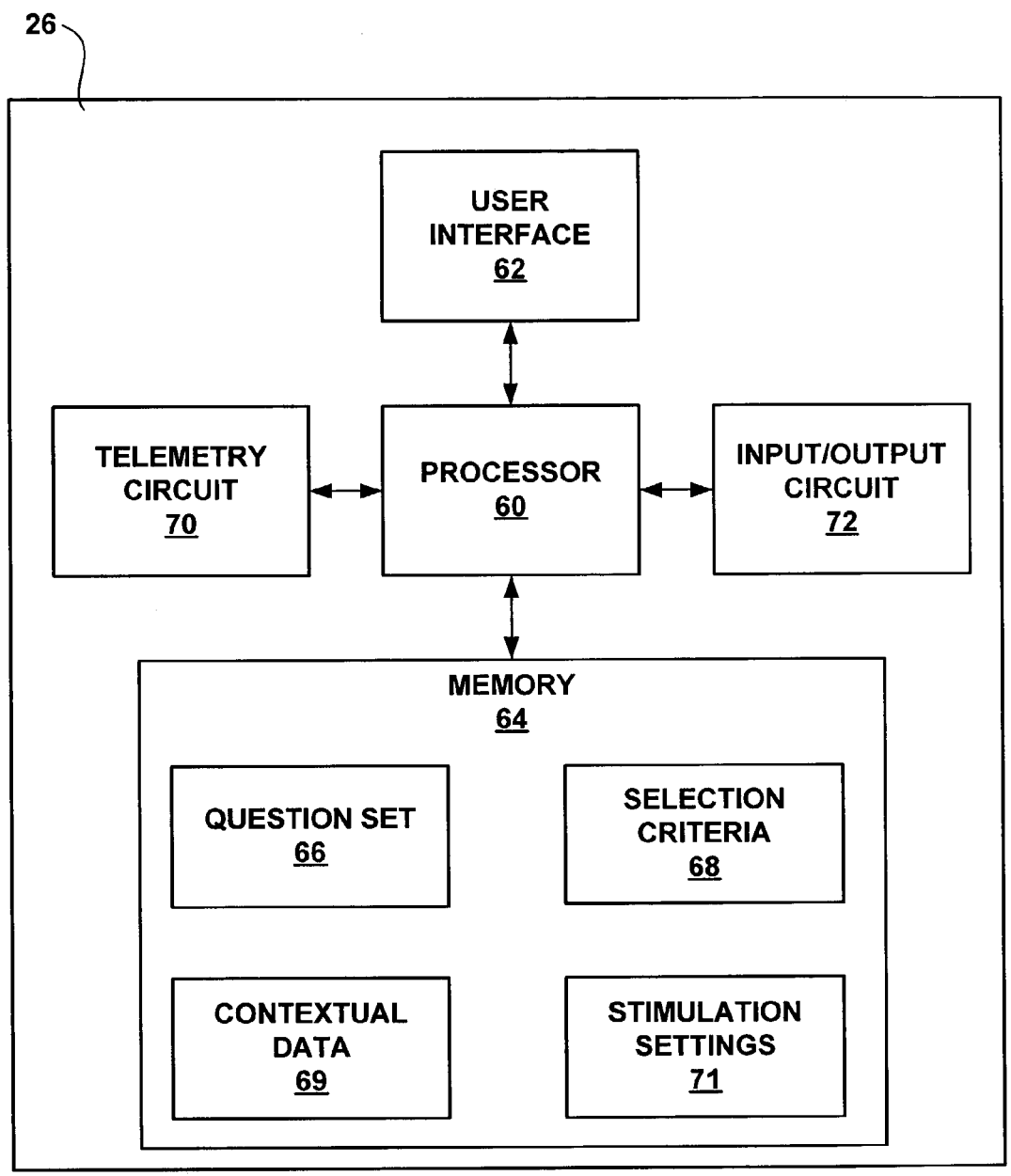
FIG. 3 is a block diagram illustrating an example patient programmer that allows a patient to control delivery of neurostimulation therapy by an implantable medical device and collects neurostimulation therapy data based on user input.

FIG. 3 is a block diagram illustrating an example configuration of patient programmer 22. Patient 12 may interact with a processor 60 via a user interface 62 in order to enter neurostimulation therapy requests and thereby control delivery of neurostimulation therapy by IMD 14. User interface 62 may include display 28 and input keys 32, 34, 36 (FIG. 1), and may also include a touch screen or peripheral pointing devices as described above. Processor 60 may also provide a text-based interface or a graphical user interface (GUI) to facilitate interaction with patient 12, as will be described in greater detail below. Processor 60 may include a microprocessor, a controller, a DSP, an ASIC, an FPGA, discrete logic circuitry, or the like.

Patient programmer 22 also includes a memory 64. Memory 64 may include program instructions that, when executed by processor 60, cause patient programmer 22 to perform the functions ascribed to patient programmer 22 herein, including preparation and presentation of context-sensitive questions. Memory 64 may include any volatile, non-volatile, fixed, removable, magnetic, optical, or electrical media, such as a RAM, ROM, CD-ROM, hard disk, removable magnetic disk, memory cards or sticks, NVRAM, EEPROM, flash memory, and the like.

In addition, memory 64 may store question set 66, selection criteria 68, contextual data 69 and stimulation settings 71. Question set 66 may contain a set of questions formulated by a clinician for presentation to patient 12 via patient programmer 22. Selection criteria 68 maps questions in question set 66 to specific neurostimulation therapy contexts. Accordingly, upon determination of a particular context, processor 60 accesses selection criteria 68 to select particular questions from question set 66 for presentation to patient 12. As an alternative, question set 66 may contain groups of questions that are prearranged according to context. In this case, processor 60 selects a prearranged group of questions rather than selecting individual questions to form a group.

Stimulation settings 71 may contain different programs for selection by patient 12 including different combinations of amplitude, pulse width, pulse rate, duration, electrode selection, and the like. Patient programmer 22 stores usage information in contextual data 69 for analysis by a clinician. In particular, contextual data 69 include answers to the questions presented by patient programmer 22 and information indicative of the neurostimulation therapy context at the time the questions were presented.

Patient programmer 22 also includes a telemetry circuit 70 that allows processor 60 to communicate with IMD 14, and input/output circuitry 72 to allow processor 60 to communicate with clinician programmer 20. Processor 60 may receive parameter set selections made by patient 12 via user interface 62, and may either transmit the selection or the selected parameter set to IMD 14 via telemetry circuit 70 for delivery of neurostimulation therapy according to the selected parameter set. Where patient programmer 22 stores parameter sets 66 in memory 64, processor 60 may receive parameter sets 66 from clinician programmer 20 via input/output circuitry 72 during programming by a clinician. Circuitry 72 may include transceivers for wireless communication, appropriate ports for wired communication or communication via removable electrical media, or appropriate drives for communication via removable magnetic or optical media.

Figure 4:
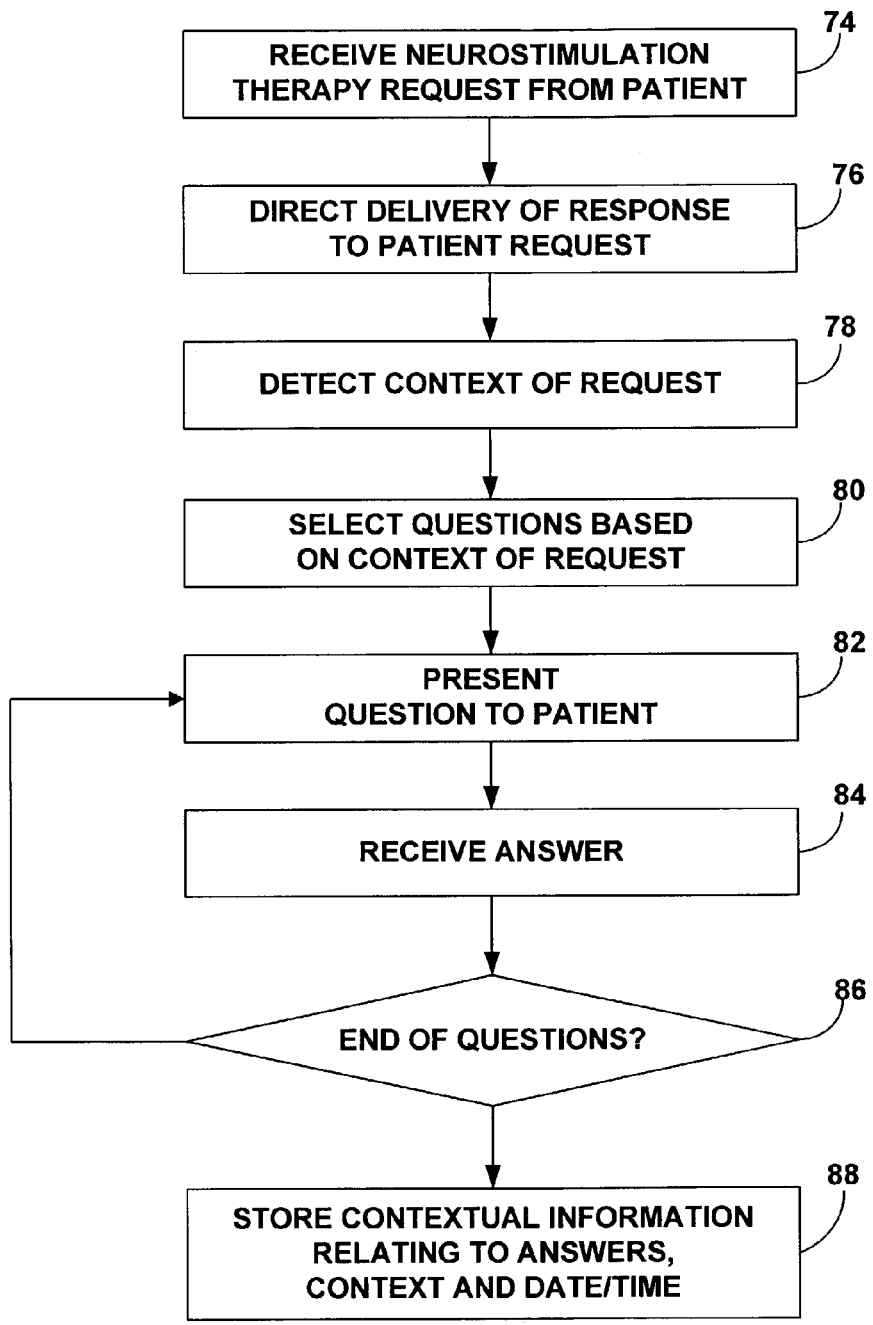
FIG. 4 is a flow diagram illustrating a method for context-sensitive collection of neurostimulation therapy data.

FIG. 4 is a flow diagram illustrating a method for context-sensitive collection of neurostimulation therapy data. The method depicted in FIG. 4 may be performed in conjunction with a patient programmer 22 as described herein. In particular, patient 12 may carry patient programmer 22 with him as he conducts his daily routine. In this manner, patient 12 may make neurostimulation therapy requests and answer context-sensitive questions presented by patient programmer 22. Patient programmer 22 stores the resulting contextual data for analysis by the clinician.

As shown in FIG. 4, upon receiving a neurostimulation therapy request from patient 12 (74), patient programmer 22 may direct delivery of a response to the patient request (76). The neurostimulation therapy request may include a request to start, stop or adjust neurostimulation therapy, and may be entered via input keys 32, 34, 36 (FIG. 1). Accordingly, delivery of a response may include communicating a command to IMD 14 to start delivery, stop delivery, or adjust one or more stimulation settings. Alternatively, in some cases, patient programmer 22 may direct IMD 14 to deliver a "placebo" response. In particular, patient programmer 22 may not actually deliver the requested response, but instead do nothing. In each case, patient programmer 22 detects the context of the neurostimulation request entered by the user (78), and selects a set of one or more questions based on the context of the request (80).

Patient programmer 22 presents each question to patient 12 (82), e.g., via display 28 (FIG. 1). Patient 12 then enters an answer to the question. Patient programmer 22 may receive the answer via any of input keys 32, 34, 36 (84), or via a touch screen or other suitable input media. When patient programmer 22 reaches the end of the questions selected for the applicable context (86), the patient programmer stores the information relating to the answers entered by patient 12, as well as information indicative of the context and date/time information, within memory 64 as contextual data 69 (88).

The contextual information may indicate the particular stimulation settings applied by IMD 14 or requested by patient 12, and the date and time at which the neurostimulation therapy request is made. Again, the neurostimulation therapy request may be a request to start therapy, stop therapy or modify settings for therapy being delivered to the patient. Thus, the neurostimulation therapy request may be as simple as a request to increase stimulation amplitude.

Figure 5:
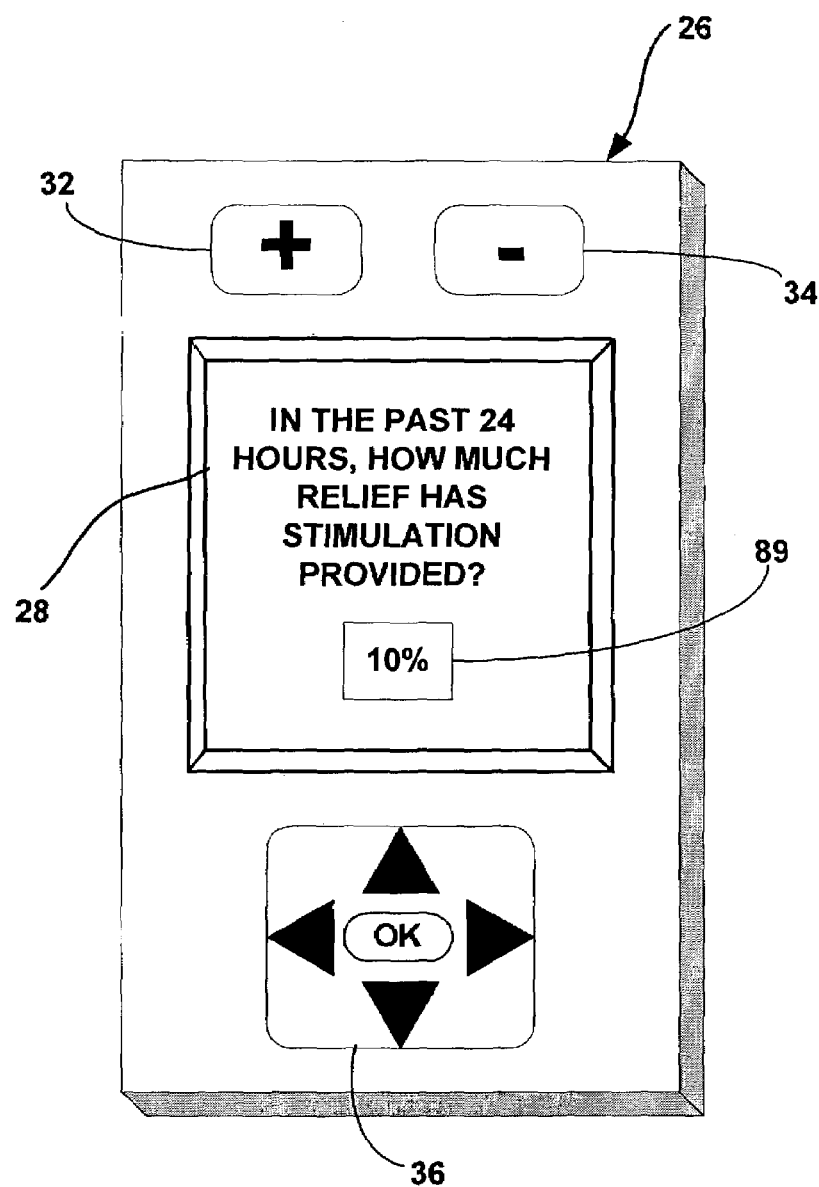
FIG. 5 is a conceptual diagram of a patient programmer used for context-sensitive collection of neurostimulation therapy data.

FIG. 5 is a conceptual diagram of a patient programmer 22 used for context-sensitive collection of neurostimulation therapy data. FIG. 5 shows patient programmer 22 substantially as depicted in FIG. 1. As shown in FIG. 5, input key 32 may permit patient 12 to increase (+) stimulation amplitude, while input key 34 may permit the patient to decrease (−) stimulation amplitude. In the example of FIG. 5, display 28 presents a question: "IN THE PAST 24 HOURS, HOW MUCH RELIEF HAS STIMULATION PROVIDED?" Display 28 further presents a percentage field by which patient 12 may enter an answer to the question, e.g., 10% relief (89). Input keys 32, 34 may permit patient 12 to increase or decrease the percentage in order to effectively answer the question. Input key 36 may permit patient 12 to navigate between different regions of display 28, e.g., to select particular answers to questions or change settings. The particular size, shape and configuration of input keys 32, 34, 36 of FIG. 5 are purely for purposes of example, and should not be considered limiting of the invention as broadly embodied and described herein.

A wide variety of context-sensitive questions may be formulated by the clinician. For pain therapy, for example, patient programmer 22 may include sets of context-sensitive questions relating the following topics:

1. Medication Log. Context-sensitive questions for this topic may seek information concerning the number of times in which the patient has taken pain medication in a period of time, such as the previous 24 hours. In addition, the questions may ask the patient to assess how much relief the medication has provided, e.g., 10%, 20%, . . . 90%, 100%.

2. Quality of Life and Activity Level. Context-sensitive questions for this topic may seek information concerning the impact of pain on the patient's activities. For example, the questions could include a request to rate activity level on a scale, e.g., "Please rate your ability to perform the following activities: walking, sleeping, lifting, climbing, and bending" or "Please rate your overall quality of life."

3. Site of Worst Pain and Associated Visual Analog Scale. Context-sensitive questions for this topic may seek information concerning the site of pain experienced by the patient, including rating scale information indicating the intensity of the pain for different areas such as the shoulder, lower back, left leg, and right leg."

4. McGill-Melzack Pain Questionnaire. Context-sensitive questions for this topic may seek information concerning the quality of pain experienced by the patient. For example, the questions may request that the patient characterize the pain with qualifiers such as "throbbing, shooting, stabbing, sharp, burning, dull, or tender."

5. Pain Relief. Context-sensitive questions for this topic may seek information concerning efficacy of neurostimulation therapy, including information about the benefit or level of satisfaction provided to the patient by the therapy. An example question is depicted in FIG. 5: "In the past 24 hours, how much relief has stimulation provided?" The patient could answer the question with a percentage of relief.

For movement disorders, the questions presented to patient 12 may seek information relating to efficacy of therapy in suppressing symptoms such as arm, leg, head, or other tremor, rigidity, arm, leg, head, or other akinesia, arm, leg, head, or other bradykinesia, or gait problems. The questions may seek information relating to the severity of side effects of therapy, e.g., arm, leg, head, or other dyskinesia, arm, leg, head, or other paresthesia, diplopia, dysarthria, dizziness, salivation, mood alteration, or the like. Also, the questions may be designed to obtain information about complementary therapy regimes, such as drug dosing, schedules, changes in dosage, and the like. The questions may ask the patient to rate the level of symptoms such as tremor, bradykinesia, dyskinesia, or the like. Some questions could quantify the level by percentages or affirmative answers, e.g., "When stimulation is on, I experience: (a) no dyskinesia, (b) non-troublesome dyskinesia, (c) troublesome dyskinesia." Questions relating to movement disorders could also include medication log and activity level/quality of life questions.

Figure 6:
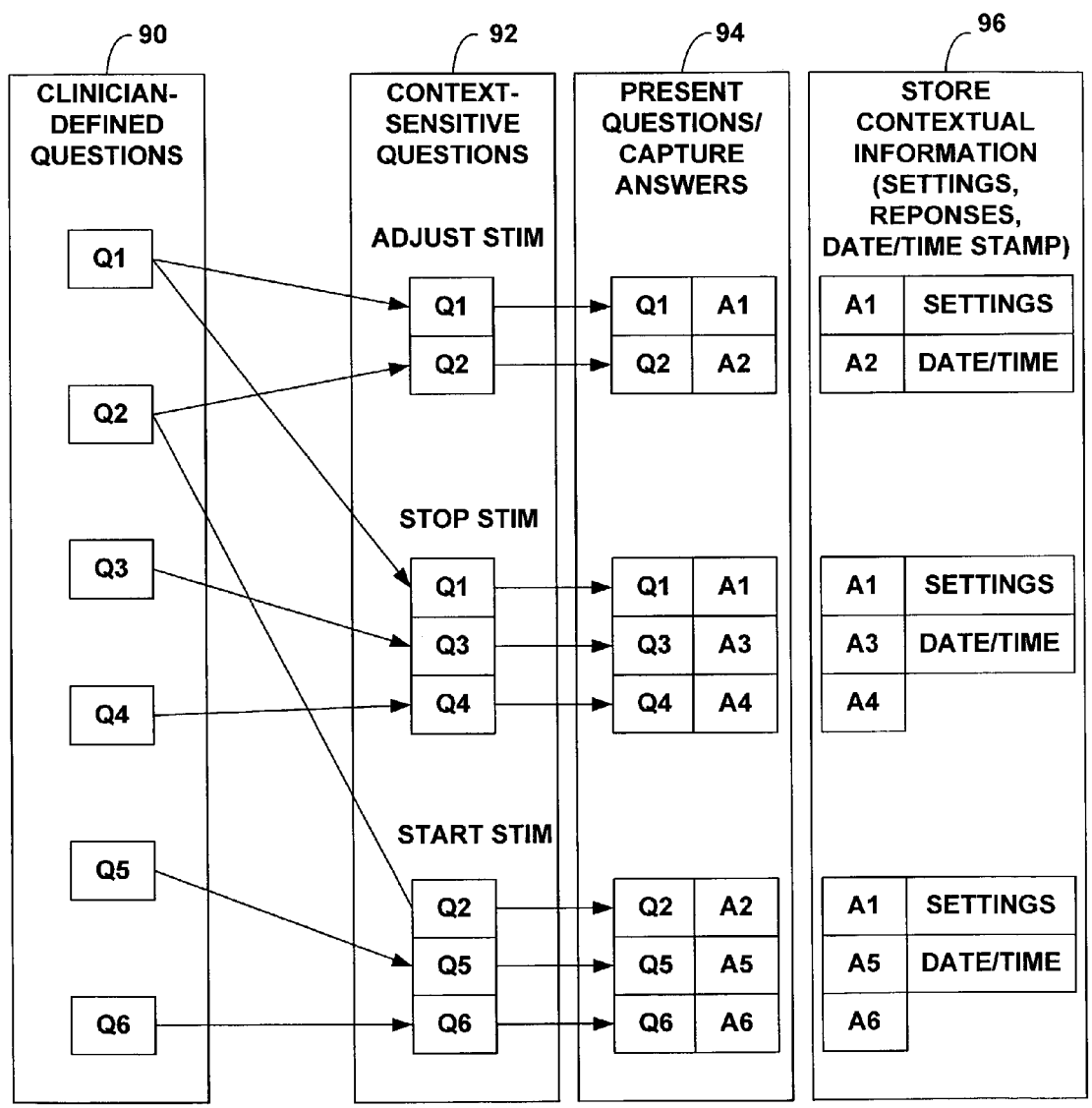
FIG. 6 is a flow diagram illustrating generation of context-sensitive questions and storage of information in response to the questions.

FIG. 6 is a flow diagram illustrating generation of context-sensitive questions and storage of information in response to the questions. As shown in FIG. 6, upon determination of a context associated with a neurostimulation therapy request, patient programmer 22 selects questions from a set of clinician-defined questions (90). Again, the questions may be formulated by a clinician and stored in memory 64 of patient programmer 22, either individually or in predefined contextual groups.

For example, if the context involves a request by patient 12 to adjust stimulation settings, patient programmer 22 may select questions Q1 and Q2. If the context involves stopping stimulation, patient programmer 22 may select questions Q1, Q3 and Q4. Similarly, if the context involves starting stimulation, patient programmer 22 may select questions Q2, Q5, and Q6. In this manner, patient programmer 12 prepares a set of context-sensitive questions (92) for presentation to patient 12.

Patient programmer 12 may present the context-sensitive questions in conjunction with a response to the patient's neurostimulation therapy request or in conjunction with a placebo response. Upon presentation of the questions and receipt of context-sensitive answers A1-A6 (94), patient programmer 22 stores context-sensitive data (96) in memory associated with patient programmer 22. The context-sensitive data may include the applicable context, answers received from patient 12 for the context, stimulation settings applicable to the existing neurostimulation therapy, stimulation setting adjustments requested by the patient, and date and time information associated with the request.

Techniques as described herein permit a patient programmer 22 or other device to select questions residing in memory based on a context associated with operation of an IMD 14 that provides neurostimulation therapy to patient 12. In general, patient programmer 22 responds to a patient-activated event such as a neurostimulation therapy request, administers the requested therapy or a placebo, and configures a set of context-sensitive questions. It may be desirable to obtain answers to the questions before delivery of a response to the request, following delivery of the response, or both. Obtaining the answers after delivery of the response may be more useful in evaluating the effect of the response on the patient.

The clinician may load memory 64 of patient programmer 22 with questions selected from a standard set of questions. Alternatively, the clinician may select desired questions from the standard set. In particular, the clinician may tailor the questions to a patient's individual pattern of symptoms or to predictable profiles of pain or other symptoms. In either case, patient programmer 12 assembles the questions in sets of questions suitable for particular neurostimulation therapy requests such as start, stop or adjust requests. In addition, the questions may be selected according to the time of day when the questions are presented, i.e., in view of known symptom profiles for the patient or class of patient. D The use of context-sensitive questions in system 10 may permit timely assessment and documentation of pain or other symptoms, as well as side effects. In addition, patient programmer 22 may be configured to present questions selected to capture pain scores for the purpose of describing the patient pain profile and assessing therapy efficacy. The stored information may form a comprehensive record of the patient's utilization of the neurostimulation therapy for specific symptoms, and may support trend analysis of therapy utilization data.

As an added feature, the delivery of either active or placebo responses on a selective basis may permit the questions to be formulated for randomized study design. The clinician can use the resulting context-specific information obtained by patient programmer 22 to tailor neurostimulation therapy programs for the individual patient 12.

In addition to prompting the patient for input at appropriate times, patient programmer 22 may include an event marking feature that permits patient 12 to log therapeutically significant events at arbitrary times. The events could be selected from a fixed list or could be created or customized by a clinician. Types of events that might be marked include breakthrough symptoms such as pain, tremor or the like, changes in side effects, medication dosing, or activities that impact therapy such as exercise, sleep, or posture changes. These types of events may form part of the context-specific information stored in contextual data 69 within memory 64.

The clinician may subsequently correlate the event logs with therapy settings in effect at the time of the event. Such correlation analyses could be used to increase the efficacy of the therapy. For example, the clinician may determine that a particular stimulation setting yields fewer breakthrough pain events or side effects than another stimulation setting. In some embodiments, the context-specific contextual data 69, including logged events, may be uploaded to clinician programmer 20 or another computing device to permit the clinician to more effectively analyze the data. For example, clinician programmer 20 or another computing device may be configured to display logged events, correlation analyses, and resulting therapy recommendations based on the analyses for clinician use.

The invention may provide a number of advantages. As explained herein, use of context-sensitive questions may offer effective collection of diagnostic data in the context of patient usage of neurostimulation therapy. The data can be correlated with a patient's schedule and activities, and with particular disease states and associated characteristics. In addition, the data can be collected throughout the course of a patient's daily routine, e.g., via a handheld patient programmer device.

The data may offer greater precision and be used to build a base of clinical information for use by the clinician in establishing improved neurostimulation therapy efficacy. For example, the data may be used to synchronize therapy efficacy with a patient's schedule and activities, provide an individualized approach to treatment of pain and other disorders.

Use of the resulting data may lead to reduced stimulation of undesired sites, increased patient satisfaction, and reduced programming time, including less clinician time required to position paresthesia. In some cases, fewer office visits to the clinician may be required, and trial trial-and-error reprogramming efforts may be reduced.

Various embodiments of the invention have been described. However, one skilled in the art will appreciate that various modifications may be made to these embodiments without departing from the scope of the invention. These and other embodiments are within the scope of the following claims.

The invention claimed is:

1. A patient programmer device for use by a patient for programming a neurostimulation device implanted within the patient comprising:
  an input interface that receives a neurostimulation therapy control request from the patient to control delivery of neurostimulation therapy by the neurostimulation device to the patient, wherein the therapy control request includes an adjustment to the neurostimulation therapy;

a processor that detects a context associated with the request and selects one or more questions based on the detected context associated with the request, wherein the processor selects one or more different questions based on different detected contexts; and an output interface that presents the selected questions to the patient.

2. The device of claim 1, wherein the processor selects a series of questions based on the context associated with the request.

3. The device of claim 2, wherein the processor obtains answers to the questions, and stores information relating to the answers, the context associated with the request, and one or more settings associated with neurostimulation therapy associated with the request.

4. The device of claim 3, wherein the settings include pulse amplitude, pulse width, and pulse rate.

5. The device of claim 3, wherein the information further includes a date and time of the answers.

6. The device of claim 3, wherein the input interface receives additional therapy control requests, and at least some of the additional therapy control requests include requests to start delivery of the neurostimulation therapy or requests to stop delivery of the neurostimulation therapy, and wherein the information relating to the context associated with the request indicates whether the request included an adjustment to the neurostimulation therapy, a request to start the neurostimulation therapy, or a request to stop the neurostimulation therapy.

7. The device of claim 3, wherein the processor stores the information in a memory associated with a neurostimulation device programmer.

8. The device of claim 1, wherein the input interface receives additional therapy control requests, and at least some of the additional therapy control requests include a request to start delivery of the neurostimulation therapy and a request to stop delivery of the neurostimulation therapy.

9. The device of claim 8, wherein the processor directs delivery of a response to each of the requests.

10. The device of claim 9, wherein the processor directs delivery of a response by directing one of delivering neurostimulation therapy to the patient, modifying one or more parameters associated with neurostimulation therapy delivered to the patient, and delivering a placebo neurostimulation therapy to the patient.

11. The device of claim 1, wherein the questions include a question relating to intake of medication by the patient, a question relating to a level of activity by the patient, a question relating to specification of one or more sites of pain within the patient, and a query relating to a degree of pain relief achieved by neurostimulation therapy associated with the request.

12. The device of claim 11, wherein the questions further include a question relating to a quality of pain experienced by the patient.

13. The device of claim 1, wherein the questions include a question relating to one of a pain syndrome and a movement disorder.

14. The device of claim 1, wherein the questions are formulated by a clinician responsible for care of the patient.

15. The device of claim 1, further comprising a memory that stores context-sensitive questions and selection criteria to select one or more of the context-sensitive questions based on a context associated with the request.

16. The device of claim 15, wherein the selection criteria maps the context-sensitive questions to specific neurostimulation contexts.

17. The device of claim 1, wherein the patient programmer device is a handheld, portable patient programmer device.

18. The device of claim 1, wherein the neurostimulation therapy request includes selection of a program that specifies a combination of stimulation settings for the neurostimulation device implanted within the patient.

19. The device of claim 18, wherein the combination of stimulation settings comprises a combination of a duration, an amplitude, a pulse width, and a pulse rate.

20. The device of claim 1, wherein the neurostimulation therapy request includes selection of a program that specifies a combination of electrodes of the neurostimulation device implanted within the patient.

21. The device of claim 1, wherein the processor controls a therapy delivery circuit of the neurostimulation device implanted within the patient to delivery neurostimulation therapy to the patient.

22. The device of claim 21, wherein the processor controls the therapy delivery circuit to deliver electrical pulses via a selected subset of electrodes of the neurostimulation device having selected polarities.

23. The device of claim 1, wherein the adjustment to the neurostimulation therapy includes a request to modify settings for neurostimulation therapy associated with the request.

24. A computer-readable medium comprising instructions to cause a processor of a patient programmer device for use by a patient for programming a neurostimulation device implanted within the patient to:

receive a neurostimulation therapy control request from the patient to control delivery of neurostimulation therapy by the neurostimulation device to the patient, wherein the therapy control request includes an adjustment to the neurostimulation therapy;

detect a context associated with the request;

select one or more questions based on the detected context associated with the request, wherein the instructions cause the processor to select one or more different questions based on different detected contexts; and present the selected questions to the patient.

25. The computer-readable medium of claim 24, wherein the instructions cause the processor to select a series of questions based on the context associated with the request.

26. The computer-readable medium claim 25, wherein the instructions cause the processor to:

obtain answers to the questions; and store information relating to the answers, the context associated with the request, and one or more settings associated with neurostimulation therapy associated with the request.

27. The computer-readable medium of claim 26, wherein the settings include pulse amplitude, pulse width, and pulse rate.

28. The computer-readable medium of claim 26, wherein the information further includes a date and time of the answers.

29. The computer-readable medium of claim 26, wherein the instructions cause the processor to receive additional therapy control requests, and at least some of the additional therapy control requests include requests to start delivery of the neurostimulation therapy or requests to stop delivery of the neurostimulation therapy, and wherein the information relating to the context associated with the indicates whether the included an adjustment to the neurostimulation therapy associated with the request, a request to start the neurostimulation therapy, or a request to stop the neurostimulation therapy.

30. The computer-readable medium of claim 26, wherein the instructions cause the processor to store the information in a memory associated with a neurostimulation device programmer.

31. The computer-readable medium of claim 24, wherein the instructions cause the processor to receive additional therapy control requests, and at least some of the additional therapy control requests include a request to start delivery of the neurostimulation therapy and a request to stop delivery of the neurostimulation therapy.

32. The computer-readable medium of claim 24, wherein the questions include a question relating to intake of medication by the patient, a question relating to a level of activity by the patient, a question relating to specification of one or more sites of pain within the patient, and a query relating to a degree of pain relief achieved by neurostimulation therapy associated with the request.

33. The computer-readable medium of claim 32, wherein the questions further include a question relating to a quality of pain experienced by the patient.

34. The computer-readable medium of claim 24, wherein the questions include a question relating to one of a pain syndrome and a movement disorder.

35. The computer-readable medium of claim 24, wherein the questions are formulated by a clinician responsible for care of the patient.

36. The computer-readable medium of claim 24, wherein the instructions cause the processor to direct delivery of a response to each of the requests.

37. The computer-readable medium of claim 36, wherein the instructions cause the processor to direct delivery of a response to the request by directing one of delivering neurostimulation therapy to the patient, modifying one or more parameters associated with neurostimulation therapy delivered to the patient, and delivering a placebo neurostimulation therapy to the patient.

38. The computer-readable medium of claim 24, wherein the adjustment to the neurostimulation therapy includes selection of a program that specifies a combination of stimulation settings for the neurostimulation device implanted within the patient.

39. The computer-readable medium of claim 24, wherein the adjustment to the neurostimulation therapy includes selection of a program that specifies a combination of electrodes of the neurostimulation device implanted within the patient.

40. A patient programmer device for use by a patient in which a neurostimulation device is implanted, the patient programmer device comprising:
an input interface that receives a neurostimulation therapy control request from a patient, wherein the therapy control request instructs the patient programmer device to adjust neurostimulation therapy delivered by the implanted neurostimulation device, start delivery of the neurostimulation therapy, or stop delivery of the neurostimulation therapy;
a processor that detects a context associated with the request, wherein the context includes a type of the request, and selects one or more questions based on the detected context including the type of the request from the patient, wherein the processor selects one or more different questions based on different detected contexts including based on the different types of request; and
an output interface that presents the selected questions to the patient.

41. The patient programmer device of claim 40, wherein the processor obtains answers to the questions, and stores information relating to the answers, the context associated with the request, and one or more settings associated with neurostimulation therapy associated with the request.

42. The patient programmer device of claim 41, wherein the settings include pulse amplitude, pulse width, and pulse rate.

43. The patient programmer device of claim 41, wherein the information relating to the context associated with the request indicates whether the type of request included a request to adjust the neurostimulation therapy, start delivery of the neurostimulation therapy, or stop delivery of the neurostimulation therapy.

44. The patient programmer device of claim 40, wherein the questions include a question relating to intake of medication by the patient, a question relating to a level of activity by the patient, a question relating to specification of one or more sites of pain within the patient, and a query relating to a degree of pain relief achieved by neurostimulation therapy associated with the request.

45. The patient programmer device of claim 40, wherein the patient programmer device is a handheld, portable patient programmer device.

46. A handheld, portable patient programmer device for use by a patient for controlling an implantable neurostimulation device that delivers neurostimulation therapy to the patient, the device comprising:
an input interface that receives from the patient an adjustment to the neurostimulation therapy delivered by the implantable neurostimulation device;
a processor that controls the neurostimulation device to make the adjustment, detects a context associated with the adjustment in response to the adjustment received from the patient, and selects one or more questions based on the context, wherein the processor selects one or more different questions based on different detected contexts;
an output interface that presents the selected questions to the patient, wherein the input interface receives answers to the selected questions; and
a memory that stores information relating to the answers, the context associated with the adjustment, and one or more settings associated with neurostimulation therapy associated with the request.

47. The patient programmer device of claim 46, wherein the adjustment to the neurostimulation therapy includes selection of a program that specifies a combination of stimulation settings for the neurostimulation device.

48. The patient programmer device of claim 46, wherein the adjustment to the neurostimulation therapy includes selection of a program that specifies a combination of electrodes of the neurostimulation device.

49. A patient programmer device for use by a patient for programming a neurostimulation device implanted within the patient comprising:
means for receiving a neurostimulation therapy control request from the patient to control delivery of neurostimulation therapy by the neurostimulation device to the patient, wherein the therapy control request includes an adjustment to the neurostimulation therapy;
means for detecting a context associated with the request;
means for selecting one or more questions based on the detected context associated with the request, wherein the means for selecting selects one or more different questions based on different detected contexts; and means for presenting the selected questions to the patient.

50. A patient programmer device for use by a patient for programming a neurostimulation device implanted within the patient comprising:

an input interface that receives neurostimulation therapy control requests from the patient, wherein at least some of the therapy control requests include adjustments to the neurostimulation therapy delivered by the neurostimulation device;

a processor that controls the neurostimulation device based on the therapy control requests received from the patient, detects a context associated with the request and selects one or more questions based on the detected context associated with the request, wherein the processor selects one or more different questions based on different detected contexts; and an output interface that presents the selected questions to the patient.

* * * * *

UNITED STATES PATENT AND TRADEMARK OFFICE
CERTIFICATE OF CORRECTION

| | | |
|---|---|---|
| PATENT NO. | : 7,647,116 B2 | |
| APPLICATION NO. | : 10/388798 | |
| DATED | : January 12, 2010 | |
| INVENTOR(S) | : Ruth E. Bauhahn | |

It is certified that error appears in the above-identified patent and that said Letters Patent is hereby corrected as shown below:

Title page, item (*) Notice:  should read as follows:  Subject to any disclaimer, the term of this patent is extended or adjusted under 35 U.S.C. 154(b) by 1404 days.

Col. 12, Line 19: "to delivery neurostimulation" should read --to deliver neurostimulation--

Signed and Sealed this

Seventh Day of September, 2010

David J. Kappos
*Director of the United States Patent and Trademark Office*